US00PP34198P2

(12) United States Plant Patent
Kamstra

(10) Patent No.: US PP34,198 P2
(45) Date of Patent: May 3, 2022

(54) POINSETTIA PLANT NAMED 'EURZ0021'

(50) Latin Name: *Euphorbia pulcherrima*
Varietal Denomination: EURZ0021

(71) Applicant: SYNGENTA CROP PROTECTION AG, Basel (CH)

(72) Inventor: Silvan Adelmar Kamstra, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/155,309

(22) Filed: Jan. 22, 2021

(51) Int. Cl.
*A01H 6/38* (2018.01)
*A01H 5/02* (2018.01)

(52) U.S. Cl.
USPC ..... Plt./307

(58) Field of Classification Search
USPC ..... Plt./307
See application file for complete search history.

*Primary Examiner* — Annette H Para
(74) *Attorney, Agent, or Firm* — Dale Skalla

(57) ABSTRACT

A new Poinsettia plant named 'EURZ0021' particularly distinguished by the distinct red bract color, dark green foliage, and strong vigor with very good branching and strong stems.

1 Drawing Sheet

Latin name of the genus and species of the plant claimed: *Euphorbia pulcherrima.*

Varietal denomination: 'EURZ0021'.

BACKGROUND OF THE NEW PLANT

The present invention comprises a new Poinsettia, botanically known as *Euphorbia pulcherrima*, and hereinafter referred to by the variety name 'EURZ0021'.

'EURZ0021' is a product of a designed crossing between a plant called '37888' and 's90-0241-01'. The new cultivar has bright red bract color. The variety has large size inflorescences with bracts a little upright directed, dark green foliage, and very strong vigor with good branching.

'EURZ0021' originates from cross made in 2015 in Enkhuizen, The Netherlands.

A greenhouse crop was developed from the first selected plant and evaluated. These plants were multiplied separately and examined in Enkhuizen, The Netherlands in 2017 and later years in the fall-winter flowering for uniformity and stability of the new combination of characteristics.

BRIEF SUMMARY OF INVENTION

Horticultural examination of plants grown in Enkhuizen, The Netherlands from cuttings of the plant initiated in April 2017, and continuing thereafter, has demonstrated that the combination of characteristics as herein disclosed for 'EURZ0021' are firmly fixed and are retained through successive generations of asexual reproduction.

'EURZ0021' has not been observed under all possible environmental conditions. The phenotype may vary significantly with variations in environment such as temperature, light intensity and day length.

A Plant Breeder's Right for this cultivar was applied for in the European Union on Dec. 1, 2020, No. 2020/3151. 'EURZ0021' has not been made publicly available prior to the effective filing date of this application, notwithstanding any disclosure that may have been made less than one year prior to the effective filing date of this application by the inventor or another who obtained 'EURZ0021' directly from the inventor.

The following traits have been repeatedly observed and are determined to be basic characteristics of the new variety. The combination of these characteristics distinguishes this Poinsettia as a new and distinct variety.

BRIEF DESCRIPTION OF THE PHOTOGRAPHS

The accompanying photographic drawing shows typical flower and foliage characteristics of 'EURZ0021' with colors being as true as possible with an illustration of this type. The photographic drawings show flowering potted plants of the new variety.

Figure 1:
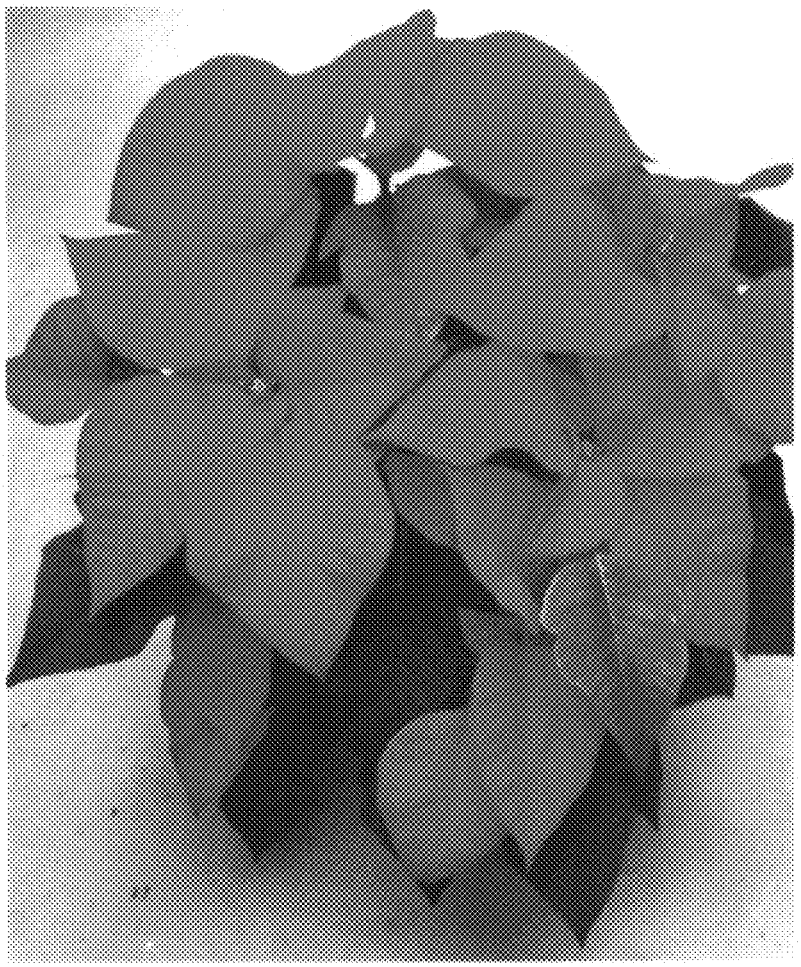

FIG. 1 was taken on Nov. 26, 2020 and shows a side view of the plant, on a plant about 20 weeks old.

Figure 2:
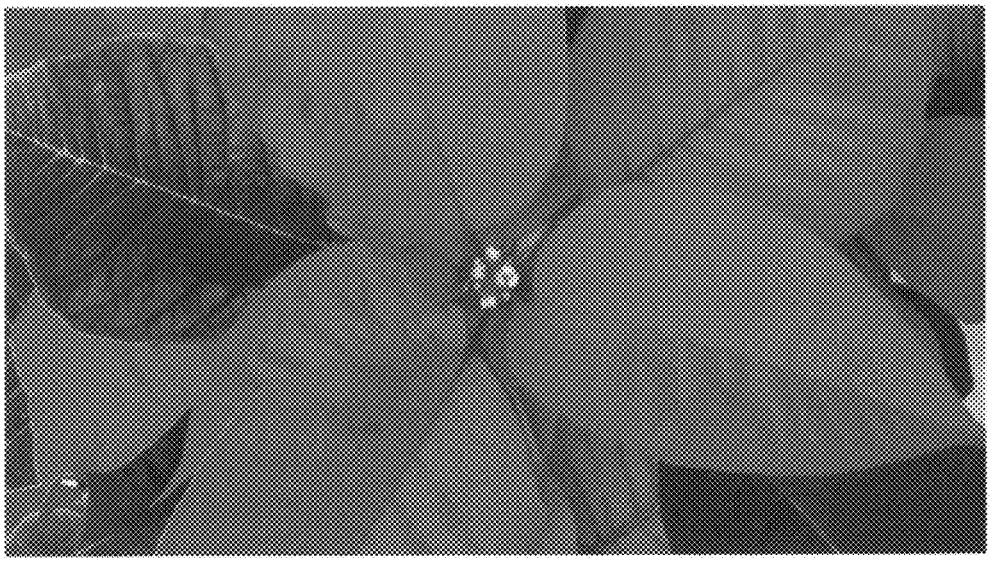

FIG. 2 was taken on Nov. 26, 2020 and shows a close-up view of the bracts.

DETAILED BOTANICAL DESCRIPTION

The measurements were taken in Enkhuizen, The Netherlands in December 2020 on 21 weeks old plants growing in a greenhouse. Culture of these plants had started in late June 2020 with planting rooted cuttings in 13 cm pots and terminal pinching about 2 weeks later. The plants were grown under natural day light in the fall (no black cloth to initiate earlier flowering) and at the moderately warm temperature of 18°-20° C. for the bench heating. No use of PGR.

Color references are made to The Royal Horticultural Society Colour Chart (R.H.S.) 2001.

TABLE 1

DIFFERENCES BETWEEN THE NEW VARIETY 'EURZ0021' AND A SIMILAR VARIETY

| | 'EURZ0021' | 'EURZ0009' (U.S. Plant Pat. No. 30,545) |
|---|---|---|
| Plant height: | 35 cm | 30 cm |
| Cyathia size: | 0.4 cm | 0.6 cm |
| Bract color: | RHS 45C/45B | RHS 45B |

Plant:

*Form, growth and habit.*—Shrub, with the branches slanting upright, good branching.

*Plant height (inflorescence included).*—35-40 cm.

*Plant width.*—35-40 cm.

Roots:

*Number of days to initiate roots.*—18-20 days at about 24 degrees C.

*Number of days to produce a rooted cutting.*—24-26 days at 24 degrees C.

*Type.*—Fine, fibrous, free branching.

*Color.*—RHS N155C.

Foliage:

*Arrangement.*—Alternate, 8-11 leaves per branch.

*Immature, leaf color, upper surface.*—Approximately RHS 139A.

*Lower surface.*—RHS 147A.

*Mature, leaf color, upper surface.*—RHS 139A.

*Lower surface.*—RHS 147A.

*Length.*—10-12 cm.

*Width.*—8-11 cm.

*Shape.*—Ovate, with almost no lobes.

*Base shape.*—Obtuse to rounded.

*Apex shape.*—Acuminate.

*Margin.*—Entire; lobes, when present mostly rounded.

*Aspect.*—Leaf blades are slightly downwards directed.

*Texture, upper surface.*—Smooth.

*Lower surface.*—Smooth, apart from the protruding veins.

*Color of veins, upper surface.*—RHS 147B and very light RHS 183D for the central vein at base, turning to RHS 147B towards the leaf tip.

*Color of veins, lower surface.*—Central vein RHS 183D turning to RHS 147B towards the leaf tip.

*Petiole color, upper surface.*—RHS 187B-C.

*Lower surface.*—RHS 184A.

*Length.*—5-8 cm.

*Diameter.*—0.30 cm.

*Aspect.*—Slightly upward directed.

*Texture.*—Glabrous.

Stem:

*Quantity of main branches per plant.*—About 6 to 8.

*Color of stem.*—RHS 147B with slightly RHS 183B.

*Length of stem.*—20-23 cm.

*Diameter.*—0.6-0.8 cm.

*Length of internodes.*—1.5-3 cm.

*Texture.*—Glabrous.

*Color of peduncle.*—RHS 144B to RHS 144C.

*Length of peduncle.*—0.2-0.3 cm.

*Peduncle diameter.*—0.2 cm.

*Texture.*—Glabrous.

Inflorescence:

*Type.*—Terminal cyme with surrounding whorl of colored bracts.

*Flowering, botanically (opening of the stamen, shedding of pollen).*—Late November.

*Flowering, commercially (sufficiently colored bracts).*—Mid November.

*Flowering response time.*—About 7.5-8 weeks from equinox.

*Duration of flowering.*—Depends on light and environment, at least 4-6 weeks of shelf life.

*Fragrance.*—Absent.

*Shape of inflorescence.*—Rosette-like whorl, star-shaped; bracts borne nearly horizontally to weakly funnel-shaped (slanting upright); tight center.

*Diameter of inflorescence.*—30 cm.

*Inflorescence, vertical diameter.*—5-8 cm.

*Number of completely colored bracts per inflorescence (sized over 2 cm).*—7-9.

*Single bract, shape.*—Ovate with relatively long, pointed tips, without weak lobes.

*Bract, apex.*—Acuminate.

*Bract, base.*—Weakly rounded.

*Single bract, length of blade.*—Up to 14 cm, younger bracts diminishing in size.

*Single bract, width of blade.*—Up to 10 cm, younger bract diminishing in size.

*Bract color, upper side.*—RHS 45B/45C.

*Bract color, lower side.*—RHS 45C.

*Vein color, upper surface.*—RHS 45B.

*Vein color, lower surface.*—Approximately RHS 45B.

*Texture.*—Weakly rugose, glabrous.

*Bract petiole color, upper surface.*—RHS 185A.

*Bract petiole color, lower surface.*—RHS 187C.

*Bract petiole, length.*—About 4 cm, shorter with younger bracts.

*Bract petiole diameter.*—0.2-0.3 cm.

Cyme (true inflorescence):

*Cyme, diameter.*—1.0-1.5 cm.

*Number of cyathia.*—5, borne in a tight cluster.

*Cyathium, shape.*—Ovate.

*Cyathium, diameter.*—0.2-0.4 cm.

*Cyathium, length.*—0.4-0.5 cm.

*Color.*—RHS 143B, top is RHS 53B.

*Nectar cups.*—Usually 2 per cyathium.

*Nectur cup, width.*—0.3 cm.

*Nectar cup, color.*—RHS 18A/144C.

Reproductive organs:

*Stamen (actually reduced male florets).*—Usually in a small bunch of 5-10 at the top of the cyathium.

*Shape.*—Strap-like.

*Filament length.*—0.2 cm.

*Filament color.*—RHS 53B-C.

*Anther color.*—RHS 46A.

*Anther diameter.*—0.1 cm.

*Pollen quantity.*—Moderate (normal quantity).

*Pollen color.*—RHS 12A.

*Female flowers.*—Not yet observed.

*Fertility/seed set.*—Has not been observed on this plant.

Disease/pest resistance: Disease/pest resistance has not been observed on this plant.

What is claimed is:

1. A new and distinct variety of Poinsettia plant named 'EURZ0021', substantially as illustrated and described herein.

* * * * *